United States Patent [19]
Gurvich et al.

[11] 4,087,469
[45] May 2, 1978

[54] METHOD OF PRODUCING 2,2'-METHYL-ENEBIS(4,6-DIALKYLPHENOLS)

[76] Inventors: Yakov Abramovich Gurvich, Sretensky bulvar, 6, kv. 61; Alexandr Afroimovich Grinberg, Khalturinskaya ulitsa, 10, korpus 2, kv. 30, both of Moscow; Alexandr Grigorievich Liakumovich, ulitsa Galeeva, 10, kv. 8, Kazan; Jury Ivanovich Michurov, prospekt Lenina, 13, kv. 4, Sterlitamak Bashkirskoi ASSR; Olga Fedorovna Starikova, Rublevskoe shosse, 89, korpus 2, kv. 52, Moscow; Vladimir Avgustovich Yanshevsky, ulitsa Kommunisticheskaya, 42, kv. 12, Novokuibyshevsk; Simona Tevievna Kumok, Poklonnaya ulitsa, 4, kv. 32, Moscow; Evgeny Lvovich Styskin, Khalturinskaya ulitsa, 10, korpus 2, kv. 48, Moscow; Grigory Iosifich Rutman, ulitsa Revoljutsionnaya, 7, kv. 6, Sterlitamak Bashkirskoi ASSR, all of U.S.S.R.

[21] Appl. No.: 641,595

[22] Filed: Dec. 16, 1975

[51] Int. Cl.$^2$ .................. C07C 37/00; C07C 37/20
[52] U.S. Cl. .................................................. 568/723
[58] Field of Search ..................... 260/619 A

[56] References Cited

U.S. PATENT DOCUMENTS

| | | | |
|---|---|---|---|
| 2,602,821 | 7/1952 | Luten et al. | 260/619 A |
| 2,675,366 | 4/1954 | Pullman | 260/619 A |
| 3,037,946 | 6/1962 | Guest et al. | 260/619 A |
| 3,057,928 | 10/1962 | Koblitz et al. | 260/619 A |
| 3,584,061 | 6/1971 | Olstowski et al. | 260/619 A |
| 3,761,525 | 9/1973 | Young et al. | 260/619 A |
| 3,919,330 | 11/1975 | Kwantes et al. | 260/619 A |
| 3,920,573 | 11/1975 | Vegter et al. | 260/619 A |
| 3,972,950 | 8/1976 | Kwantes | 260/619 A |

OTHER PUBLICATIONS

Karrar, "Organic Chemistry", p. 153, (1947), Elsurer.
Moller, "Chem. of Org. Comp", pp. 228–229, 1965, Saunders.

*Primary Examiner*—Norman Morgenstern
*Attorney, Agent, or Firm*—Haseltine, Lake & Waters

[57] ABSTRACT

A method of producing 2,2'-methylenebis(4,6-dialkylphenols) residing in that 2,4-dialkylphenols interact with acetals in the presence of an acid catalyst at a temperature from 30° C to 140° C with the formation of a reaction mixture containing the desired product and with subsequent separation of the desired product from said mixture, the starting reagents being taken in amounts of 1 mole of 2,4-dialkylphenol per 1–10 moles of acetal.

The method is technologically simple and accomplished without the formation of waste water.

2 Claims, No Drawings

METHOD OF PRODUCING 2,2'-METHYLENEBIS(4,6-DIALKYLPHENOLS)

The present invention relates to producing 2,2'-methylenebis(4,6-dialkylphenols).

2,2'-methylenebis(4,6-dialkylphenols) are effective stabilizers of polymer materials. They protect almost all kinds of polymers from ageing, do not affect their colour, and are nonvolatile. Thus, for example, 2,2'-methylenebis(4-methyl-6-tert.butylphenol), the most important stabilizer of this class, is widely used to protect rubbers, resins, polyolefins, chloro- and nitrogen-containing polymers, polyoxymethylene, polysterene and other polymers against thermal oxidation.

Known in the art are batch processes of producing 2,2'-methylenebis(4,6-dialkylphenols) based on emulsion condensation of 2,4-dialkylphenols with a condensing agent. For example, formaldehyde is used as a condensing agent. Condensation is run in the presence of an acid catalyst, for example, sulphuric acid. The process is carried out in a water emulsion of 2,4-dialkylphenol containing a surfactant and an organic solvent at a temperature from 75° to 90° C. The main disadvantage of this process is the formation of waste water in large amounts, contaminated with the surfactant and organic solvents.

In other sources, a method of producing 2,2'-methylenebis(4,6-dialkylphenols) is described consisting in condensation of 2,4-dialkylphenols with formaldehyde in an organic solvent at a temperature from 90° to 110° C. The method fails to ensure the high yield of pure product. The formation of waste water is not excluded either since formaldehyde is used as a 37% aqueous solution.

In some methods, paraform is used as the condensing agent, but the desired product obtained in low yield and of poor quality. Condensation with trioxymethylene is performed in an aqueous solution of formic acid. Therefore, the formation of waste water is also possible.

Likewise known in the art is a method of producing 2,2'-methylenebis(4,6-dialkylphenols) by water-emulsion condensation of 2,4-dialkylphenols with a 36% aqueous solution of formaldehyde as the condensing agent.

As 2,4-dialkylphenols use is made, for example, of 4-methyl-2-tert.butylphenol, 4-ethyl-2-tert.butylphenol, 4-ethyl-2-tert.octylphenol.

The reaction is carried out in the presence of an organic solvent, for example, heptane, chlorobenzene, a surfactant, and sulphuric acid as a catalyst.

The reaction temperature is maintained within a range from 30° to 140° C, for example, 75°–90° C.

As a result, a mixture is obtained containing the desired product. The mixture is neutralized with sodium hydrate solution and the desired product is isolated by known methods, such as filtration or centrifugation.

The yield of the desired product is 96–98%.

The method is disadvantageous in that waste water is used in large amounts containing impurities of the organic solvent and the surfactant: 12,000–15,000 liters of waste water are formed per 1 ton of the desired product.

The same disadvantage is inherent in a known continuous method of producing 2,2'-ethylenebis(4-methyl-6-tert.butylphenol), based on water-emulsion condensation of 4-methyl-2-tert.butylphenol with formaldehyde.

It is an object of the invention to provide a method of producing 2,2'-methylenebis(4,6-dialkylphenols) which will preclude waste water formation, ensuring high yield of a high quality end product.

In accordance with these and other objects, the invention consists in that a method is proposed of producing 2,2-methylene bis(4,6-dialkylphenols) by interacting 2,4-dialkylphenols with a condensing agent in the presence of an acid catalyst at a temperature from 30° to 140° C with the formation of a reaction mixture containing the desired product and with subsequent isolation of the product from said mixture.

According to the invention, acetals are used as the condensing agent and the starting reagents are taken in amounts of 1 mole of 2,4-dialkylphenol per 1–10 moles of acetal.

As the catalyst, use can be made of sulphuric, phosphoric, perchloric, toluene sulphonic and other mineral or organic acids, as well as cation exchange resins, for example, sulphated copolymer of styrene with divinylbenzene.

The reaction can be carried out in a wide temperature range from 30° to 140° C.

The reaction proceeds in an acetal medium which is both a condensing agent and a solvent. Therefore, it is taken in amounts of 1–10 moles per 1 mole of 2,4-dialkylphenol (preferably 4–5 moles); stoichiometric relationship is 0.5 mole of acetal per 1 mole of 2,4-dialkylphenol. Excess acetal not participating in the reaction is removed and used in subsequent syntheses.

As acetals it is recommended to use, for example, methylal, diethylformal, dimethylformal, dimethylacetal, diethylacetal, diisopropylacetal and the like.

Condensation of 2,4-dialkylphenols with acetals allows the production of 2,2-methylenebis(4,6-dialkylphenols) not only in a batch process, but also continuously, without the formation of waste water and waste products. The yield of 2,2'-methylenebis(4,6-dialkylphenols) obtained by this method is as high as 98%. The products are of high quality. Thus, for example, 2,2'-methylenebis(4-methyl-6-tert.butylphenol) has a melting point of no less than 128°–129° C.

The method is technologically simple. No new equipment is required for its implementation.

Due to the use of acetals, the reaction proceeds in a solution. Thus, there is no need to introduce surfactants into the reaction mixture.

The proposed method is realized as follows.

2,4-dialkylphenol is dissolved in acetal and the solution is stirred in the presence of catalytic amounts of an acid catalyst, for example, sulphuric, phosphoric acids, sulphates copolymer of styrene with divinylbenzene, and the like.

The reaction may be carried out over a wide temperature range from 30° to 140° C. As a result, a reaction mixture is obtained containing the desired product. The mixture is then cooled, the catalyst is neutralized and removed. When sulphated copolymer of styrene with divinylbenzene is used as the catalyst, it is removed from the reaction mixture just after cooling this mixture. Next, the unreacted acetal is distilled off from said mixture and the desired product is delivered, in the form of a melt, for flaking.

For a better understanding of the present invention specific examples are given hereinbelow by way of illustration.

EXAMPLE 1

82 g of 4-methyl-2-tert.butylphenol, 200 ml of methylal, and 2.5 g of concentrated sulphuric acid are put into a reactor fitted with a thermometer, a condenser, and a stirrer.

The contents of the reactor are stirred for 2 hrs at 60°–70° C. Then the obtained reaction mixture is cooled to 20° C, calcium oxide is added for neutralization of sulphuric acid, and after stirring for another 20 min, the mixture is filtrated. The unreacted methylal is distilled off from the filtrate. The residue is 2,2'-methylenebis(4-methyl-6-tert.butylphenol), m.p. 128°–129° C. The yield of the product is 98% of theory.

EXAMPLE 2

60 g of cation-exchange resin (sulphated copolymer of styrene with divinylbenzene) and a solution of 82 g of 4-methyl-2-tert.butylphenol in 180 ml of methylal are put into the reactor described in Example 1. The contents of the reactor is stirred for 3 hrs at 30°–70° C. The obtained reaction mixture is cooled to 20° C, the catalyst is separated by filtration, and the unreacted methylal is distilled off from the filtrate.

The product obtained is analogous to that in Example 1. The yield is 97% of theory.

EXAMPLE 3

103 g of 2,4-ditert.butylphenol, 220 ml of methylal, and 3 g of concentrated sulphuric acid are put into the reactor described in Example 1. The contents of the reactor are stirred for 1.5 hrs at 80°–100° C.

Subsequent treatment of the obtained reaction mixture and isolation of the desired product are performed as specified in Example 1.

2,2'-methylenebis(4,6-ditert.butylphenol) is obtained, m.p. 141°–142° C. The yield of the product is 98% of theory.

EXAMPLE 4

A 30% solution of 4-methyl-2-tert.butylphenol in methylal is passed through two tubular reactors in series filled with a cation-exchange resin similar to that described in Example 2.

The temperature in the first reactor is 50°–60° C, and in the second, 70°–80° C. The solution is passed at a rate of 50–60 ml per hr. After the second reactor, the unreacted methylal is removed from the obtained reaction mixture. The residue is 2,2'-methylenebis(4-methyl-6-tert.butylphenol), m.p. 129°–130° C. The yield of the product is 99% of the theory. The distilled methylal is recycled for the preparation of a solution of 4-methyl-2-tert.butylphenol.

EXAMPLE 5

82 g of 4-methyl-2-tert.butylphenol, 300 ml of diethylformal and 2.5 g of concentrated sulphuric acid are put into the reactor described in Example 1. The contents of the reactor are stirred for 2.5 hrs at 85°–95° C. Subsequent treatment of the obtained reaction mixture and separation of the desired product are performed following the procedure described in Example 1.

2,2'-methylenebis(4-methyl-6-tert.butylphenol) is produced, m.p. 128°–129° C, in yield 86% of theory.

EXAMPLE 6

60 g of a cation-exchange resin of the kind described in Example 2 and a solution of 82 g of 4-methyl-2-tert.butylphenol in 250 ml of diethylformal are put into the reactor described in Example 1. The contents of the reactor are stirred for 4 hrs at 85°–95° C. Subsequent treatment of the obtained reaction mixture and isolation of the desired product are performed following the procedure described in Example 2.

2,2'-methylenebis(4-methyl-6-tert.butylphenol) is produced, m.p. 128°–129° C. The yield of the product is 92% of theory.

EXAMPLE 7

82 g of 4-methyl-2-tert.butylphenol, 250 ml of dimethylacetal and 2.5 g of concentrated sulphuric acid are put into the reactor described in Example 1. The contents of the reactor are stirred for 2.5 hrs at 64°–70° C. Subsequent treatment of the obtained reaction mixture and separation of the desired product are carried out following the procedure described in Example 1.

2,2'-ethyledenebis(4-methyl-6-tert.butylphenol) is produced, m.p. 104°–105° C. The yield of the product is 80% of theory.

EXAMPLE 8

103 g of 2,4-ditert.butylphenol, 300 ml of diethylformal and 3 g of concentrated sulphuric acid are put into the reactor described in Example 1. The contents of the reactor are stirred for 2.5 hrs at 85°–95° C. Subsequent treatment of the obtained reaction mixture and separation of the desired product are performed following the procedure described in Example 1.

2,2'-methylenebis(4,6-ditert.butylphenol), m.p. 141°–142° C, is obtained in 75% yield of theory.

EXAMPLE 9

82 g of 4-methyl-2-tert.butylphenol, 400 ml of diethylacetal, and 2.5 g of concentrated sulphuric acid are put into the reactor described in Example 1. The contents of the reactor are stirred for 3 hrs at 103°–110° C. Subsequent treatment of the obtained reaction mixture and separation of the desired product are performed following the procedure described in Example 1.

2,2'-ethyledenebis 4-methyl-6-tert.butylphenol) is obtained, m.p. 104°–105° C. The yield of the product is 70% of theory.

EXAMPLE 10

61 g of 2,4-xylenol, 400 ml of diisopropylacetal, and 2.5 g of concentrated sulphuric acid are put into the reactor described in Example 1. The contents of the reactor are stirred for 3 hrs at 82°–90° C. Subsequent treatment of the obtained reaction mixture and separation of the desired product are performed following the procedure described in Example 1.

2,2'-methylenebis(4,6-dimethylphenol) is produced, m.p. 125°–126° C, in 85% yield of theory.

EXAMPLE 11

61 g of 2,4-xylenol, 220 ml of methylal, and 2.5 g of phosphoric acid are put into the reactor described in Example 1. The contents of the reactor are stirred for 3 hrs at 95°–110° C.

Subsequent treatment of the obtained reaction mixture and separation of the desired product are performed following the procedure described in Example 1.

2,2'-methylenebis(4,6-dimethylphenol) is produced, m.p. 125°–126° C, in 83% yield of theory.

EXAMPLE 12

82 g of 4-methyl-2-tert.butylphenol, 250 ml of dimethylacetal, and 3 g of toluene sulphonic acid are put into the reactor described in Example 1. The contents of the reactor are stirred for 2.5 hrs at 75°–80° C. Subsequent treatment of the reaction mixture and separation of the desired product are performed following the procedure described in Example 1.

2,2'-ethylenebis(4-methyl-6-tert.butylphenol) is produced, m.p. 104°–105° C, in 82% yield of theory.

EXAMPLE 13

82 g of 4-methyl-2-tert.butylphenol, 200 ml of methylal, and 3.5 g of perchloric acid are put into the reactor described in Example 1. The contents of the reactor are stirred for 3 hrs at 30°–40° C. Subsequent treatment of the obtained reaction mixture and separation of the desired product are carried out following the procedure described in Example 1.

2,2'-methylenebis(4-methyl-6-tert.butylphenol) is produced, m.p. 128°–129° C, in 85% yield of theory.

EXAMPLE 14

60 g of a cation-exchange resin similar to that described in Example 2 and a solution of 87 g of 4-ethyl-2-tert.butylphenol in 200 ml methylal are put into the reactor described in Example 1. The contents of the reactor are stirred for 3 hrs at 80°–85° C. Subsequent treatment of the obtained reaction mixture and separation of the desired product are performed following the procedure described in Example 2.

2,2'-methylenebis(4-ethyl-6-tert.butylphenol) is produced, m.p. 123°–125° C, in 81% yield of theory.

EXAMPLE 15

93 g of 4-methyl-2-cyclohexylphenol, 220 ml of methylal, and 3 g of concentrated sulphuric acid are put into the reactor described in Example 1. The contents of the reactor are stirred for 2 hrs at 85°–95° C. Subsequent treatment of the obtained reaction mixture and separation of the desired product are performed by following the procedure described in Example 1.

2,2'-methylenebis(4-methyl-6-cyclohexylphenol) is produced m.p. 118°–119° C, in 90% yield of theory.

EXAMPLE 16

60 g of a cation-exchange resin similar to that used in Example 2 and a solution of 82 g of 4-methyl-2-tert.butylphenol in 75 ml of methylal are put into an airtight steel reactor fitted with a stirrer. The contents of the reactor are stirred for 1 hr at 135°–140° C. Then, the reactor is opened. Subsequent treatment of the obtained reaction mixture and separation of the desired product are carried out following the procedure described in Example 2. 2,2'-methylenebis(4-methyl-6-tert.butylphenol) is produced, m.p. 129–130° C, in 99% yield of theory.

What is claimed is:

1. A process for the preparation of 2,2-methylenebis(4,6-dialkylphenols) which process consists essentially of reacting 2,4-dialkylphenol with an acetal selected from the group consisting of dimethylformal, diethylformal, dimethylacetal, diethylacetal and diisopropylacetal in the presence of an acid catalyst at a temperature of from 30° to 140° C. at a mole ratio of 1 mole of 2,4-dialkylphenol per 1–10 moles of acetal and separating the desired product from said mixture.

2. A method as claimed in claim 1, wherein 4–5 moles of acetal per 1 mole of 2,4-dialkylphenol are used.

* * * * *